(12) United States Patent
Zimmermann et al.

(10) Patent No.: US 6,772,649 B2
(45) Date of Patent: Aug. 10, 2004

(54) GAS INLET FOR REDUCING A DIRECTIONAL AND COOLED GAS JET

(75) Inventors: Ralf Zimmermann, München (DE); Egmont Rohwer, Lynnrodene (ZA); Ralph Dorfner, Niederding (DE); Ulrich Boesl, Landshut (DE); Antonius Kettrup, Arnsberg (DE)

(73) Assignee: GSF-Forschaungszenfrum für Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 09/962,945

(22) Filed: Sep. 25, 2001

(65) Prior Publication Data

US 2002/0026821 A1 Mar. 7, 2002

Related U.S. Application Data

(63) Continuation-in-part of application No. PCT/EP00/01478, filed on Feb. 23, 2000.

(30) Foreign Application Priority Data

Mar. 25, 1999 (DE) .......................................... 199 13 451

(51) Int. Cl.$^7$ ................................................ G01N 1/00
(52) U.S. Cl. ........................ 73/863.11; 73/863; 73/23.2
(58) Field of Search ............................ 73/863.11, 863, 73/23.2, 864.81

(56) References Cited

U.S. PATENT DOCUMENTS

| | | | | |
|---|---|---|---|---|
| 4,281,246 A | * | 7/1981 | White et al. | 250/282 |
| 4,293,415 A | * | 10/1981 | Bente et al. | 210/198.2 |
| 4,376,641 A | * | 3/1983 | Nestrick et al. | 55/67 |
| 4,960,992 A | * | 10/1990 | Vestal et al. | 250/288 |
| 5,285,064 A | * | 2/1994 | Willoughby | 250/288 |
| 6,043,080 A | * | 3/2000 | Lipshutz et al. | 435/287.2 |
| 6,084,237 A | * | 7/2000 | Troster et al. | 250/288 |
| 6,390,115 B1 | * | 5/2002 | Rohwer et al. | 137/3 |

FOREIGN PATENT DOCUMENTS

EP  0 860 859   8/1998

OTHER PUBLICATIONS

Doskow J. E. et al.: "Development of Internal Jet Targets for High–Luminosity Experiments", Nuclear Instruments & Methods in Physics Research, Section—A:Accelerators, Spectrometers, Detectors and Association Equipment, N., North–Holland Publishing Company, Amsterdam, vol. A632, No. 1., Aug. 1, 1995.

Toyoda et al.: "Reactive Sputtering by SF6 Cluster Ion Beams", Nuclear Instruments & Methods in Physics Research, Section—B: Beam Interactions with Materials and Atoms, vol. 121, No. 1, 1997, pp. 484–488.

* cited by examiner

Primary Examiner—Hezron Williams
Assistant Examiner—Rodney Frank
(74) Attorney, Agent, or Firm—Klaus J. Bach

(57) ABSTRACT

In an arrangement for producing a directional and cooled gas jet in an ion source with a gas inlet or a UV/fluorescence detection cell including a gas inlet, wherein a capillary extends with one end into the interior of the ion source which is evacuated, the one end is provided with a nozzle for discharging a gas sample into the ion source while being subjected to adiabatic cooling and the width of the nozzle opening is at most 40% of the inner diameter of the capillary and the capillary is heatable for preventing condensation of gas sample components in the nozzle.

6 Claims, 3 Drawing Sheets

GAS INLET FOR REDUCING A DIRECTIONAL AND COOLED GAS JET

This is a Continuation-In-Part application of international application PCT/EP00/01478 filed Feb. 23, 2000 and claiming the priority of German application 199 13 451.0 filed Mar. 25, 1999.

BACKGROUND OF THE INVENTION

The invention resides in a gas inlet for producing a directional and cooled gas jet in an ion source or a UV/fluorescence measuring cell.

It has been common practice to introduce a gas to be analyzed into the ion source of a mass spectrometer in an effusive manner. For this purpose, an admission duct (for example, the end of a gas-chromatographic capillary) extends into the ion source. The ion source may be of closed design (for example, many CI- or EI-ion sources for quadrapole- or sector field mass spectrometers) or of an open design (for example, many ion sources for travel time mass spectrometers). In ion sources of closed design an area of the ion source is "flooded" with inlet gas so that the atoms or molecules introduced partially impinges on the walls of the ion source before they are isolated and detected in the mass spectrometer. Ion sources of open design for IOF mass spectrometers are more suitable for the employment in connection with atom- or molecular beam techniques. In that case, a relatively directed gas jet is conducted through the ion source so that, in an ideal manner, it has little interaction with the structural components of the ion source.

In the travel time mass spectroscopy, effusive molecular beams [2], as well as skimmed [1] and non-skimmed [3, 4] supersonic molecular beams are used for that purpose (in each case pulsed or continuous (cw)). Supersonic molecular beams inlet systems provide for a cooling of the analysis gas in a vacuum by adiabatic expansion. It is however disadvantageous in present systems that the expansion needs to occur relatively remote from the location of the ionization. Since the density of the expansion gas jet (and, as a result, the ion yield for a given ionization volume) decreases with the distance from the expansion nozzle in square, the achievable sensitivity is limited.

Effusive molecular beam inlet systems permit a cooling of the sample. However, gas inlet systems for effusive molecular beams cannot be so constructed that the gas discharge is directed directly to the ionization location by way of a metallic needle, which extends into the center of the ion source [2]. A certain electric potential is applied to the needle in order to avoid disturbance of the withdrawal fields in the ion source. The needle needs to be heated to relatively high temperatures in order to prevent condensation of the low-volatile analyte molecules in the needle. In this connection, it has to be taken into consideration that the coldest point should not be at the needle tip. The necessary heating of the needle is problematic since the needle must be electrically insulated with regard to all the other parts of the device (for example, by a transition piece of ceramic material). Electric insulators are generally also thermal insulators and provide for only a small heat flux of, for example, the heated duct to the needle. Heating of the needle by electric heating elements or infrared radiators is also difficult since the needle extends between the withdrawal plates of the ion source.

The selectivity of the resonance ionization by lasers (REMPI) depends on the inlet system used because of the different cooling properties of the various systems. Aside of the effusive molecular beam inlet system (EMB) which may be used, among others, for the detection of whole substance classes, it is possible to ionize highly selectively and partially even isomer-selectively by using a supersonic molecular beam inlet system (jet). With the common supersonic nozzles developed for spectroscopic experiments, the utilization of the sample amount (that is, the measuring sensitivity that can be achieved) is not a limiting factor. Furthermore, the existing systems are not designed to avoid memory effects. For the application of REMPI-TOFMS spectrometers for analytical applications, the development of an improved jet inlet technique would be advantageous. Care has to be taken that the valves consist of inert materials in order to avoid memory effects or chemical decompositions (catalysis) of the sample molecules. Furthermore, the inlet valves should not have any dead volumes. It is also necessary that the valves can be heated to temperatures of more than 200° C. so that also compounds of low volatility with a mass range>250 amu are accessible. In addition, as little sensitivity as possible should be lost by the jet arrangement as compared with the effusive inlet technique. This can be achieved mainly by a more effective utilization of the sample entered in comparison with the jet arrangements used so far.

This increase can be achieved for example in that each laser pulse reaches the largest possible part of the sample. Since the excitation volume is predetermined by the dimensions of the laser beam (a widening of the laser beam would reduce the REMPI effective cross-section which is scaled for example with a two photon ionization with the square of the laser intensity) the spatial overlap of the molecular beam (jet) and the laser beam must be optimized. This can be realized, for example, by a pulsed inlet. Boesl and Zimmerman et al., disclose for example a heatable pulsed jet valve for analytical applications, for example for a gas chromatography jet REMPI coupling with minimized dead volume [5].

Pepich et al. discloses a GC supersonic molecular jet coupling for the laser-induced fluorescence spectroscopy (LIF), wherein the duty cycle is increased over the effusive inlet by the pulsed admission and by sample compression [6].

It is the object of the present invention to provide a gas inlet of the type referred to initially which facilitates an effective cooling of a continuous gas jet with a relatively low inlet flow volume employing simple design means.

SUMMARY OF THE INVENTION

In an arrangement for producing a directional and cooled gas jet in an ion source with a gas inlet or a UV/fluorescence detection cell including a gas inlet, wherein a capillary extends with one end into the interior of the ion source which is evacuated, the one end is provided with a nozzle for discharging a gas sample into the ion source while being subjected to adiabatic cooling and the width of the nozzle opening is at most 40% of the inner diameter of the capillary and the capillary is heatable for preventing condensation of gas sample components in the nozzle.

With respect to the state of the art, the device according to the invention has the following specific advantages:

The supersonic molecular beam expansion can be selected so as to occur directly in the ion source. In this way, in principle, the highest possible density, of the gas jet 4 is achieved at the ionization location. Special advantages of the gas admission reside in the fact that the sample is cooled adiabatically, the capillary can easily be heated up to its lower end, that is its tip, and a very simple design without movable parts is achieved. The device can be so designed that the sample molecules come in contact only with inert materials. By adjustment of the appropriate parameters (gas pressure) the cooling of the gases can be realized by an adiabatic expansion into the vacuum of the mass spectrometer, (supersonic molecular jet 4), wherein generally the continuous gas flow into the ionization chamber corresponds about to that of a continuous effusive inlet (see [7]). The flow rates of effusive inlet systems are typically in the range of 0.1–100 ml/min (1 bar). In comparison with an effusive capillary inlet, in the gas inlet according to the invention the stronger orientation of the supersonic molecular jet 4 is advantageous since a better overlapping of the laser beam and the gas jet can be achieved (higher sensitivity). Particularly with the gas inlet of the type referred to earlier, a continuous, cooled gas jet can be generated also at low gas flows (<10 ml/min). As shown in FIG. 3, this can be achieved very well with the embodiment shown in FIG. 1B. A cooling of the inlet gas is advantageous for many mass spectrometric tasks. The small internal energy of cooled molecules often results in a reduced fragmentation degree in the mass spectrum. The cooling is particularly advantageous for the application of the resonance ionization with lasers (REMPI). With the use of a so-called supersonic molecular jet inlet system (Jet) for the cooling of the gas jet, it is possible with REMPI to ionize in a highly selective manner (partially even in an isomer-selective manner [1, 9]. Since the cooling occurs by the expansion, the sample gas admission conduit, the capillary 1 and the expansion nozzle 2 can be heated without detrimentally affecting the cooling properties. This is important for analytical applications. Without sufficient heating, sample components can condense in the supply conduit or in the gas inlet. An important application for the invention is the transfer of a chromatographic element of a continuous sample gas flow from an on-line sampling device into a cooled supersonic molecular jet 4. The inlet system described herein makes it possible that the expansion step occurs in the ion source of the mass spectrometer. In this way, the ions can be generated close to, or closely below, the expansion nozzle 2, which is very advantageous for the achievable detection sensitivity.

Below, the invention will be described in greater detail on the basis of the accompanying drawings.

DESCRIPTION OF PREFERRED EMBODIMENTS

Below two exemplary applications for the gas inlet according to the invention will be described. The first example concerns the application in an ion source for a mass spectrometer; the second example concerns the application in a fluorescence cell.

Figure 1:
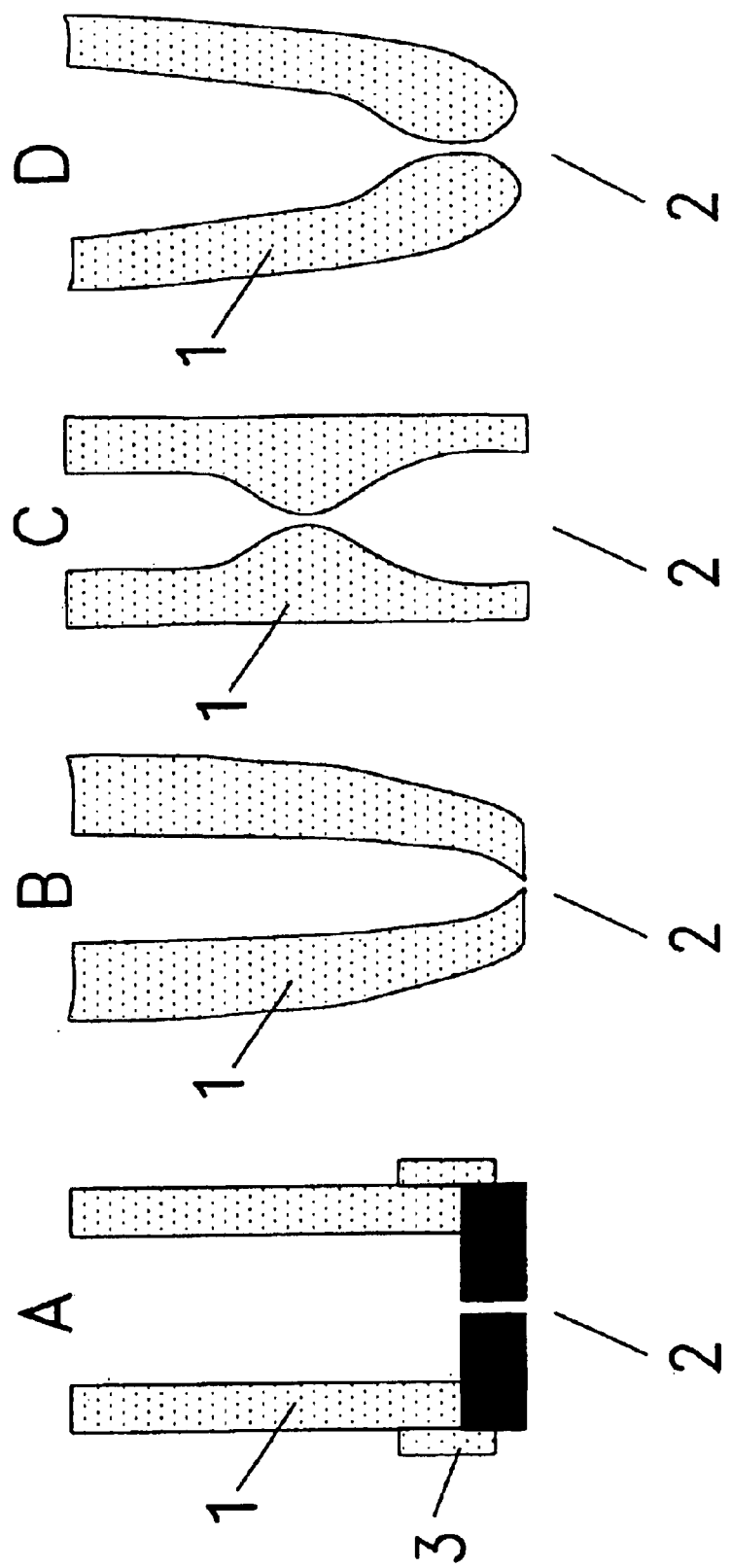
FIGS. 1A–1D show various shapes of a nozzle.
Figure 2:
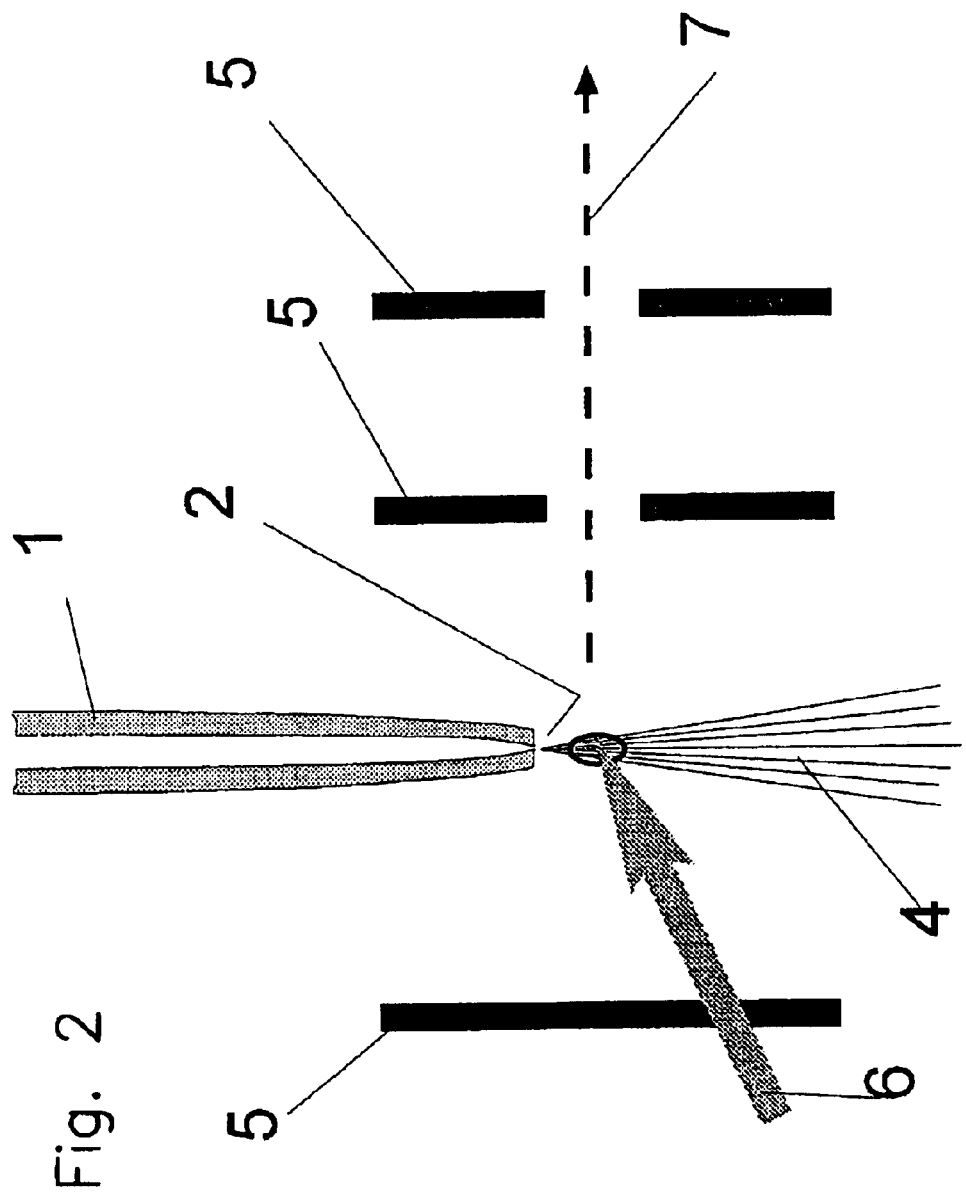
FIG. 2 shows a possible arrangement for the gas inlet in an ion source.

The capillary shown in FIGS. 1A–1D and in FIG. 2 serves for the admission of gas. It typically has an inner diameter of 0.05–10 mm. At its end, the capillary 1 has a restriction with a typical inner minimum diameter of 1–50% of the inner capillary diameter, which, below, will be called a nozzle 2. The capillary 1 is connected with its end opposite the nozzle 2 to a sample gas supply in a gas-tight manner, wherein the gas supply extends into the mass spectrometer by way of a vacuum seal. Alternatively, the end of the capillary 1 remote from the nozzle 2 may extend directly out of the vacuum chamber of the mass spectrometer for example by way of an o-ring seal (for example, with Kalrez® O-rings). The nozzle 2 is disposed within, or close to, the ion source of the mass spectrometer and has mainly two purposes: It acts as a restrictor in order to reduce the flow through the capillary 1 and to maintain in this way a good vacuum in the analysis apparatus. In addition, a supersonic molecular jet 4 is formed by the expansion into the vacuum, wherein the molecules are subjected to an adiabatic cooling. FIGS. 1A–1D show four different configurations for such a nozzle 2. In the embodiment of FIG. 1A, the capillary 1 is closed off by a disc provided with a bore to form the nozzle 2. This embodiment is suitable for all materials (glass, ceramics, quartz) for the capillary 1, but it is particularly suitable for metal capillaries 1, which may be de-activated at the inside. As metal stainless steel is particularly suitable. In this case, silanization of the metal surface is particularly suitable for deactivation. Commercially, such steel capillaries which have been made inert are available for example as Silicosteel®. As disc, for example, a saphir disc may be used. The disc is mounted for example by way of a clamping sleeve 3 or by mineral cement.

The embodiments of FIGS. 1B, C and D relate to nozzles 2, which were obtained by melting and eventually mechanical fine-cutting or grinding of one end of the capillary 1. In this case, the capillary 1 and the nozzle 2 consist of the same material, for example, quartz or glass. With capillaries 1 of metal or ceramic material, a piece of quartz or glass must be attached if a nozzle 2 of the type as shown in FIGS. 1B, 1C or 1D is to be used. The connection between capillary and nozzle can be made by a clamping sleeve 3 or by mineral cement. Alternatively, the nozzle 2 may be fused into the capillary 1. The manufacture of the embodiment of FIG. 1B is described in [8]. The embodiments of FIGS. 1C and D may be produced by carefully fusing the capillary 1 of glass or quartz with a micro-nozzle burner.

The smooth inner surface of the embodiments of FIGS. 1B, C and D is probably the reason for the high quality (that is, cooling properties) observed for the molecular jet 4 generated therewith. It is important that the pressure drop occurs essentially in the nozzle 2 in contrast to the effusive inlets by way of capillary restrictors.

For the application in an ion source, the capillary 1 is generally coated on the outside with a conductive material or is disposed within a thin metal tube through which a current can be conducted. The use of a de-activated steel (Silico steel®) is advantageous for this purpose. Steel capillaries 1 may also be directly electrically heated (resistance heating) For such an application, it is advantageous if the capillary 1 is of narrow design since, in this way, the withdrawal fields of the ion optics are subjected to less disturbances. Furthermore, an electrically conductive coating/envelope of the capillary 1 is required in order to adapt the electrical potential of the capillary 1 to the potential distribution in the ion source.

For analytical purposes, the capillary should preferably consist of quartz glass, which is deactivated on the inside in order to avoid memory effects. Ceramics and glass are also suitable materials. The open width of the nozzle should not be more than 50% of the inner diameter of the capillary. Better suitable are capillaries with a nozzle opening of 20% of the inner diameter of the capillary. The nozzle can be formed by melting or by melting and subsequent grinding of the end of the capillary. It is furthermore important that the capillary 1 is well heated up to its tip. Because of the small opening of the nozzle 2, there is the danger of clogging if sample components are condensed. In addition to resistance heating by means of electrically conductive enclosures or coatings or by optical heating via IR radiation, the capillary may also be enclosed in a thermally conductive enclosure which is heated outside of the confinements of the ion source and provides for heat transfer to the nozzle 2.

The capillary may also be heated by providing particular resistance coatings. An elegant variant is the irradiation of the capillary 1 with IR radiation, for example, by a heating element or a laser diode. In this way, the especially critical nozzle region can be very well heated.

The operation of the gas inlet according to the invention in an ion source of a travel time mass spectrometer will be described below. The narrowed end (nozzle 2) of the capillary 1 extends into the vacuum of the ion source of a mass spectrometer. The capillary consists of quartz glass and has an inner diameter of 530 $\mu$m. It is provided with a nozzle 2 of the embodiment shown in FIG. 1B with an inner diameter of 65±10 $\mu$m. The end of the capillary 1 with the nozzle 2, is guided in a thin hollow steel needle of about 3 cm length (for example, a cut injection needle), so that the tip of the nozzle 2 projects some 10 $\mu$m beyond the end edge of the steel needle. The steel needle is connected to a metal block, which is heatable by heating elements. In addition, a certain electrical potential can be applied to the needle. The analysis gas can be admitted by way of the end of the capillary 1, which extends from the vacuum housing. The capillary is sealed airtight to the housing by a graphite compression seal. The nozzle forms a gas jet in the vacuum and acts as a restrictor so that the flow through the capillary is only about 10 ml/min at 1 bar and good vacuum conditions of about $10^{-4}$ mbar are maintained in the ion source. The expansion, by way of the restriction, leads to the formation of a continuous supersonic molecular jet 4 with adiabatic cooling of the sample molecules. This adiabatic cooling is important for example for applications for increasing the selectivity of resonance-amplified multi-photon ionization mass spectrometry (REMPI-TOFMS). The capillary 1 extends in this case between the openings 5 of the ion source of the mass spectrometer. The capillary 1 with the nozzle 2 may terminate in the center of the ion source of the mass spectrometer. This is advantageous since the ionization for example by a laser beam 6 may occurs directly below or closely (for example, 1–30 mm) below the opening of the nozzle 2. The ions 7 formed in this way are withdrawn, by withdrawal apertures 5, into the travel time mass spectrometer for mass analysis. Since the density of the supersonic molecular jet 4 becomes lower in the vacuum with the square of the distance from the nozzle opening, the ionization directly below the nozzle 2 results in a substantial increase in the sensitivity.

The degree of cooling also depends on the distance form the nozzle 2 [4]. Typically, an optimal cooling can be achieved with a distance of 20 nozzle diameters below, that is, in front of, the opening of the nozzle 2. Furthermore, directly below the nozzle 2 ion-molecule reactions may occur [4]. Since the nozzle diameter of the nozzle 2 is very small (typically 0.1–200 $\mu$m) an optimal cooling can be achieved already at a distance of 2–400 $\mu$m. Furthermore, from such a distance on, a collision-free regime can be assumed (that is no ion-molecule reactions take place, which could reduce the selectivity). The ionization close to the nozzle 2 provides for a cover of the supersonic molecular jet 4 in its full width by the laser. At a speed of the supersonic molecular jet 4 of about 500 m/sec and a line-like laser profile of, for example, 4 mm×10 mm with a pulse rate of 50 Hz, with an ionization directly below the nozzle 2, a duty cycle of $10^{-3}$ is achieved (that is, each thousandth molecule in the supersonic molecular jet 4 is reached by the laser).

FIG. 2 shows schematically the arrangement of the capillary 1 with the nozzle 2 between the diaphragms of the travel time mass spectrometer.

Figure 3:
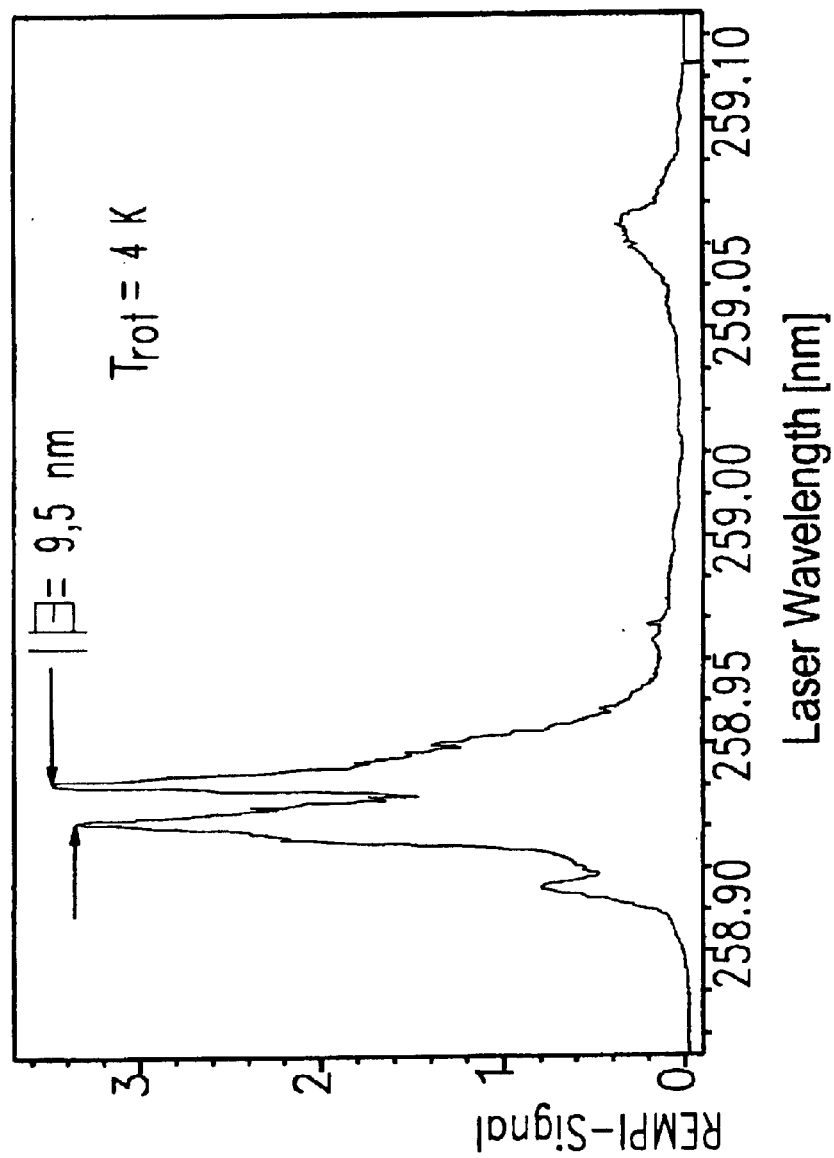
FIG. 3 shows a REMPI spectrum of benzene taken with a gas inlet according to the invention.

FIG. 3 shows a REMPI spectrum, which was recorded with the arrangement shown in FIG. 2. The REMPI spectrum of FIG. 3 shows a rotation contour of benzene. From the spectrum a rotation temperature of 4 K can be derived. This shows that very good properties of the supersonic molecular jet 4 can be achieved even with gas flows of less than 10 ml/min. The REMPI-TOFMS laser mass spectrometer with the gas inlet according to the invention may be used for example for field applications, for example, for the analysis of process gases. In comparison with the state of the art for such an application [7], the gas inlet according to the invention has the advantage of increased selectivity by the cooling of the gas jet, of low expenditures and of simple handling.

The operation of a gas inlet according to the invention in a fluorescence cell is even more simple since no consideration has to be given to the requirements of an ion lens as it is the case with an ion source for a mass spectrometer. The capillary 1 can therefore easily be provided with heating elements. It is for example possible to wind a heating wire around the capillary 1. Furthermore, there are less requirements for the vacuum system so that a highly compact and inexpensive vacuum cell, for example for field applications of the laser induced fluorescence detection (LIF) can be constructed. The fluorescence can be recorded in a wavelength dispersed (for example, with an Echelle-spectrograph and CCD detector) or an integral manner. If the excitation wavelength is in resonance, the excitation spectra can be recorded. An excitation spectrum recorded in a diperged manner is a two-dimensional spectrum (fluorescence signal as a function of the excitation and emission wavelength). As a further analytical dimension, the fadeout time of the fluorescence can be used since different compounds have different fluorescence lifetimes. The combination of a small vacuum chamber with an inlet according to the invention, an excitation laser and a fluorescence detector represents an ideal (mobile) gas analysis system for gas samples which are not excessively complex. The supersonic molecular jet 4 provides for a substantial increase of the selectivity in comparison with an effusive inlet. By utilizing characteristic absorption lines with a tunable narrow band laser (for example, a compact optical parametric oscillator, OPO) an on-line single compound analysis can be performed. In this procedure, the laser is first tuned to the absorption bands (ion resonance) and the LIF signal is measured. Then the LIF signal is determined at one or several wavelength positions where the target substance does not absorb ("off resonance"). From the differences of the "on" and "off resonance" signals the concentration of the target substance can be determined.

For relatively inexpensive process analysis with the aim to determine on-line for example a sum parameter for the fluorescent aromatics, the use of a single wavelength of for example the fourth harmonic of the Nd:Yag laser (266 nm) may be reasonable. The gas inlet according to the invention may also be used for a relatively inexpensive aromatic selective LIF detector for the gas chromatography.

In the HPLC analysis of PAK, fluorescence detection for example represents the state of the art. The utilization of the gas inlet according to the invention for a compact vacuum cell for the LIF detection would consequently provide in the gas chromatography for a detector with properties comparable to those of a HPLC fluorescence analysis but with higher selectivity and higher sensitivity. The selectivity can furthermore be adjusted by the selection of the excitation location in the supersonic molecular jet 4. Directly below the nozzle 2 the adiabatic cooling of the supersonic molecular jet 4 is not yet established. The selectivity is here relatively small. Further below the nozzle 2, the selectivity is very high because the cooling of the gas jet 4 has taken hold. The high focus of the supersonic molecular jet 4 exiting the nozzle 2 increases the sensitivity in comparison with an effusive inlet arrangement. Employing two or more wavelengths furthermore permits a discrimination between aromatics with a small and a large π system. With 266 nm (Nd:Yag) or 248 nm (KrF-Eximer) small aromatics such as benzene, toluene and xylol (BTX) or phenols as well as larger polycyclic aromatics (PAK) can be excited to fluorescence. With longer wave UV light, for example, 355 nm (third harmonic frequency of the Nd:YAG laser) BTX and comparably small aromatics are not excited whereas many larger PAK can be detected at this wavelength in a very efficient manner by way of LIF.

Description of the Figures.

FIGS. 1A–1D

Various shapes (1A to 1D) of the nozzle 2 for the capillary 1 are shown. If a disc with a bore is used as the nozzle 2 as is shown in FIG. 1A, the disc may either be cemented to the capillary or it may be attached by a clamping sleeve 3. The nozzle as shown in FIG. 1B can be made by melting to close the tip and carefully grinding the tip to re-open the nozzle. The nozzle as shown in FIG. 1C is a Laval nozzle and can be formed by a careful localized melting. The nozzle shown in FIG. 1D can be made in a similar way.

FIG. 2

This figure shows a possible arrangement of the gas inlet according to the invention in an ion source of a mass spectrometer with REMPI ionization by laser pulses 6. The capillary 1 extends between the withdrawal diaphragms 5 of the ion source. The laser beam 6 is directed into the continuous supersonic molecular jet formed in an area as close as possible to the nozzle 2. The ions formed are accelerated by the electric fields along the path 7 into the mass spectrometer for mass analysis. The supersonic molecular jet 4 is directed directly toward a vacuum pump. Not shown are the heating elements and the conductive envelope/coating of the capillary 1 as well as the transition to the vacuum with the seals.

FIG. 3

Here the REMPI spectrum of the V6 in the first excited singulette state of benzene recorded with the gas inlet according to the invention is represented. Argon with several 10% parts of benzene (1 bar) was expanded through the capillary 1 and the nozzle 2 of the form as shown in FIG. 1B into the ion source of a REMPI TOFMS mass spectrometer. The free nozzle diameter employed herein was about 65 μm with a capillary diameter of 530 μm. The gas flow rate was 9.4 ml/min, the pressure in the ion source was $5 \times 10^{-4}$ mbar. The spectrum shows the rotation contour of the v6. From the rotation contour, the rotation temperature can be determined at about 4 K [9]. This excellent rotation cooling shows that the gas inlet according to the invention provides for the generation of a continuous supersonic molecular jet 4 with good properties for analytical applications.

LITERATURE

[1] A) R. Tembreull, C. H. Sin, P. Li, H. M. Pang, D. M. Lubman; Anal. Chem. 57 (19985) 1186;
    B) R. Zimmermann, U. Boesl, C. Weickhardt, D. Lenoir, K. -W. Schramm, A. Kettrup, E. W. Schlag, Chemosphere 29 (1994) 1877
[2] A) U. Boesl, H. J. Neusser, E. W. Schlag; U.S. Pat. No. 4,433,241.
    B) R. Zimmermann, H. J. Heger, A. Kettrup, U. Boesl, Rapid. Communic. Mass Spektrom. 11 (1997) 1095
[3] H. Oser, R. Thanner, H. -H. Grotheer, Combust, Sci. And Tech. 116–117 (1996) 567
[4] R. Zimmermann, H. J. Heger, E. R. Rohwer, E. W. Schlag, A. Kettrup, U. Boesl, Proceedings of the 8th Resonance Ionization Spectroscopy Symposium (RIS-96), Penn State College 1996, AIP-Conference Proceeding 388, AIP-Press, Woobury, N.Y. (1997) 119
[5] A) DE 195 39 589.1
    B) EP 0 770 870 A2
[6] A) B. V. Pepich, J. B. Callis, D. H. Burns, M. Grouterman, D. A. Kalman, Anal. Chem. 58 (1986) 2825;
    B) B. V. Pepich. J. B. Callis, J. D. Sh. Danielson, M. Grouterman, Rev. Sci. Instrum. 57 (1986) 878.
[7] H. J. Heger, R. Zimmermann, R. Dorfner, M. Beckmann, H. Griebel, A. Kettrup, U. Boesl, Anal. Chem. 71 (1999) 46–57
[8] E. J. Guthrie, H. E. Schwartz, J. Chromatogaph. Sci. 24 (1986) 236–241
[9] R. Zimmermann, Ch. Lermer, K. W. Schramm, A. Kettrup, U. Boesl, Europ. Mass Spectrom. 1 (1995) 341–351

What is claimed is:

1. An arrangement for producing a directional and cooled gas jet in an ion source with a gas inlet or a UV/fluorescence detection cell with a gas inlet, comprising: a capillary extending into the interior of said ion source which is evacuated to generate a vacuum so that one end of said capillary is disposed in said vacuum, said one end being provided with a nozzle opening for discharging a gas sample into said ion source while being subjected to adiabatic cooling, the width of said nozzle opening being at most 40% of the inner diameter of said capillary, said capillary consisting of metal which is deactivated at the inner surface of said capillary by an inert coating and being provided with means for heating said capillary so as to prevent condensation of compounds from said sample in said nozzle.

2. An arrangement according to claim 1, wherein said inert coating is a silicon-based coating.

3. An arrangement according to claim 1, wherein the open width of said nozzle opening is less than 15% of the inner capillary diameter.

4. An arrangement according to claim 1, wherein said capillary has an inner diameter of 500±350 μm and said nozzle has a diameter of 520% of the diameter of said capillary.

5. An arrangement according to claim 1, wherein said capillary is installed in said ion source of a mass spectrometer such that the ionization occurs in the range of 0–30 mm in front of said capillary.

6. An arrangement according to claim 1, wherein the nozzle of said capillary is disposed 0–30 mm ahead of the withdrawal opening that is the ionization location of the ion source or the excitation volume of the fluorescence cell.

* * * * *